US010342248B2

(12) United States Patent
Collado et al.

(10) Patent No.: US 10,342,248 B2
(45) Date of Patent: *Jul. 9, 2019

(54) METHOD FOR THE PRODUCTION OF A POROUS POWDER PRODUCT CONTAINING A PROBIOTIC OR OTHER MICROORGANISMS

(71) Applicant: CLEXTRAL, Firminy (FR)

(72) Inventors: Maxime Collado, Pont-Salomon (FR); Jean-Marie Bouvier, Lyons (FR)

(73) Assignee: CLEXTRAL, Firminy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,622

(22) Filed: Jun. 22, 2017

(65) Prior Publication Data
US 2017/0280760 A1 Oct. 5, 2017

Related U.S. Application Data

(63) Continuation of application No. 14/407,852, filed as application No. PCT/EP2013/056127 on Mar. 22, 2013, now Pat. No. 9,763,472.

(30) Foreign Application Priority Data

Jun. 13, 2012 (EP) .................................. 12305670

(51) Int. Cl.
*A23P 10/30* (2016.01)
*A23P 10/40* (2016.01)
*A23P 30/40* (2016.01)
*A23L 33/135* (2016.01)
*C12N 1/04* (2006.01)

(52) U.S. Cl.
CPC ............. *A23L 33/135* (2016.08); *A23P 10/30* (2016.08); *A23P 10/40* (2016.08); *A23P 30/40* (2016.08); *C12N 1/04* (2013.01); *A23V 2002/00* (2013.01)

(58) Field of Classification Search
CPC ...................................................... A23P 10/40
See application file for complete search history.

(56) References Cited

U.S. PATENT DOCUMENTS 3,065,076 A   11/1962   Valentin et al.
6,010,725 A   1/2000    Meister et al.
(Continued)

FOREIGN PATENT DOCUMENTS

EP    0 063 438 A1      10/1982
WO    1998/010666 A1    3/1998
(Continued)

OTHER PUBLICATIONS

American Heritage® Dictionary of the English Language. (2011) "Foam—definition of foam by the Free Dictionary," 5th Edition. Accessible on the Internet at URL: http://www.thefreedictionary.com/foam. [Last Accessed Feb. 7, 2017].
(Continued)

*Primary Examiner* — Felicia C Turner
(74) *Attorney, Agent, or Firm* — Lathrop Gage LLP; James H. Velema, Esq.

(57) ABSTRACT

The invention proposes a method for the production of a porous powder product containing a microorganism, from a liquid concentrate comprising at least one liquid microorganism culture and a carrier composition, the carrier composition comprising at least one carbohydrate and at least one protein, the method comprising the steps of: i) preparing the liquid concentrate to have both a temperature of between and 40° C. and a viscosity greater than 150 mPa·s; ii) injecting a food grade gas into the prepared concentrate at a pressure greater than 0.3 MPa to intimately incorporate the gas into the liquid concentrate and form a stable foam with a density of between about 0.6 to about 1.2 kg/l; iii) conveying the foam to an atomizing device wherein the pressure of the foam is reduced from 0.3 MPa to atmo-
(Continued)

spheric pressure to provide a partially dried product; and iv) exposing the partially dried product to a drying media to reduce both the moisture content to less than 5% moisture and the water activity to less than 0.25 $A_w$, when measured at 20° C., and to provide the porous powder product, wherein the temperature of the porous powder product in step (iv) does not exceed 50° C.

20 Claims, 4 Drawing Sheets

(56) References Cited

U.S. PATENT DOCUMENTS 6,287,616 B1  9/2001  Beeson et al.
2005/0266069 A1  12/2005  Simmons et al.
2010/0104718 A1  4/2010  Durand et al.
2012/0282371 A1  11/2012  Miller

FOREIGN PATENT DOCUMENTS

| WO | 2001/005941 A2 | 1/2001 |
| WO | 2001/037656 A2 | 5/2001 |
| WO | 2001/044440 A1 | 6/2001 |
| WO | 2004/022031 A2 | 3/2004 |
| WO | 2005/047489 A1 | 5/2005 |

OTHER PUBLICATIONS

Derwent World Patents Index Abstract for Brazillian Patent Application No. 9303850 A, published in 1994, assigned to Lipartiti. Accession No. 1994-176822.

International Search Report corresponding to International Application No. PCT/EP2013/056127, dated May 2, 2013.

METHOD FOR THE PRODUCTION OF A POROUS POWDER PRODUCT CONTAINING A PROBIOTIC OR OTHER MICROORGANISMS

CROSS-REFERENCE TO RELATED APPLICATIONS

This application is a continuation of U.S. patent application Ser. No. 14/407,852, filed Dec. 12, 2014, which is a 35 U.S.C. § 371 filing of International Application No. PCT/EP2013/056127, filed Mar. 22, 2013, which claims priority to European Patent Application No. 12305670.7, filed Jun. 13, 2012, each of which is incorporated herein by reference in its entirety.

The invention relates to the production of porous dried powdered products containing probiotic materials or other microorganisms with high levels of viable cells.

The preparation of highly viable biological cultures has been the subject of intense research and development. One issue that continues to cause difficulties is how to process biological cultures into food products without compromising the viability of the cultures. Probiotic microorganisms are bacteria that are capable of producing a beneficial effect on the consumer when ingested in sufficient quantities and for a sufficient time. There is a strong interest in incorporating probiotics into food products to create functional food and/or nutraceuticals. It has been recommended that probiotic products contain at least $10^7$ live microorganisms per g or cfu/g (cfu is the abbreviation for "colony forming unit"), which has been difficult to achieve with existing methodology. Maintaining the viability of probiotics during the processing has proved extremely challenging and capital intensive, particular when porous powdered products are required.

One approach for processing probiotic cultures has been the use of freeze drying techniques whereby the moisture content of the culture is significantly reduced. While it is possible to prepare dried probiotic cultures with high cfu values, this technique is energy and capital intensive and requires between 24 to 48 hours per batch. This type of technique is therefore not easily amenable to large scale production without considerable capital investment.

Modern spray drying techniques are continuous processes which are used to quickly prepare many dried food products. These techniques typically involve high powder temperatures (>60° C.) which will kill most microorganisms leading to lower cfu values for the processed product. Other disadvantages with spray drying include the high energy consumption, with about 1.8 to about 3.8 kg of steam per kg of evaporated water, associated constraints in particle size management, high operating volumes (leading to a large footprint), low process flexibility and a low adaptability for processing of temperature sensitive cultures, such as probiotics and other microorganisms.

From a commercial perspective, improved methodology for the large-scale production of dried biological cultures with high cfu values is highly desirable and keenly sought. Thus, U.S. Pat. No. 6,010,725, which can be considered as the closest prior art with respect to the method defined in appended claim 1, discloses a method for the production of a porous powder product containing a probiotic. In U.S. Pat. No. 6,010,725, a liquid concentrate comprising microorganisms, protein and carbohydrate is reduced to a powder by spraying in a spray-drying device. U.S. Pat. No. 6,010,725 explains that the aforesaid device is adapted from that described in FIG. 1c of U.S. Pat. No. 3,065,076: the concentrate to be sprayed is in a liquid phase so as to be supplied through a pump and a pipeline to a spraying nozzle from which the liquid is discharged in a drying chamber. In order to promote the survival of the microorganisms in the dried powder, U.S. Pat. No. 6,010,725 proposes to select the operating parameters of the spray-drying device so that the residence time of the sprayed liquid droplets of the concentrate is adjusted to dry these droplets without rising the internal temperature of the sprayed droplets above 40 to 70° C. Just before the spraying nozzle, an inert gas may be introduced in the liquid concentrate in order to promote the spraying, that is to say the formation of the liquid droplets. In any case, the teaching of U.S. Pat. No. 6,010,725 is based on forming liquid droplets of the concentrate and to control the drying of these sprayed liquid droplets in a drying chamber. In practice, as admitted in U.S. Pat. No. 6,010,725, the implementation of the method thereof needs a fine adjustment of some operating parameters, which makes difficult and expensive a large scale production.

An object of the present invention is to propose such an improved methodology for the production of porous dried powder products containing a probiotic or other microorganisms.

To this end, the subject of the invention is a method as defined in appended claim 1. Additional advantageous features of this method are specified in the dependent claims.

Thanks to the formation of the stable foam from a prepared viscous concentrate, the porous dried product produced according the invention is not subjected to high temperatures and the log reduction of the live microorganisms is typically no more than about 1. Storage tests after three months are showing acceptable levels of survivability.

Embodiments of the invention will be better understood from reading the description which will follow, which is given solely by way of example and with the reference to the drawings in which.

Figure 1:
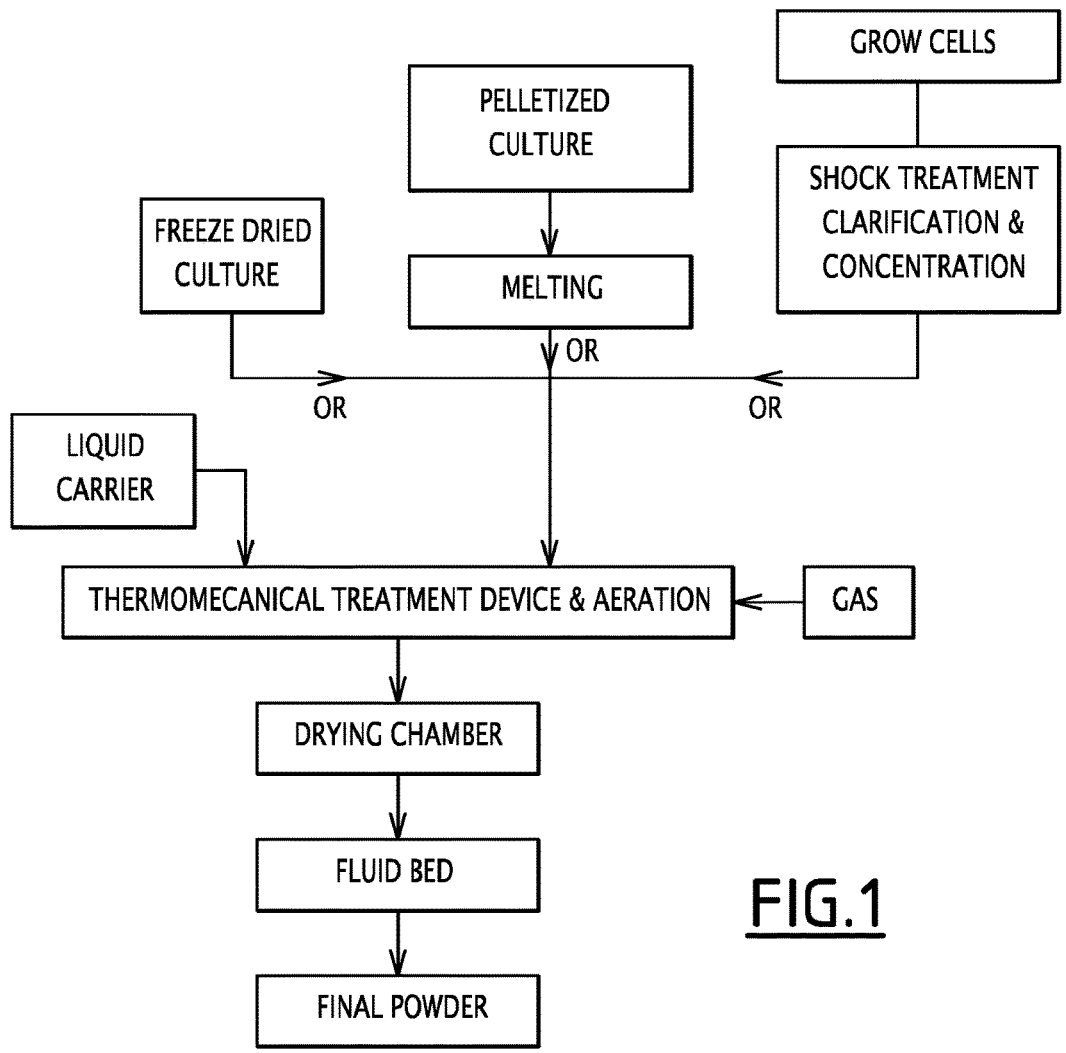
FIG. 1 is a flow chart showing a porous powder production containing cultures according the invention, where the cultures are supplied freeze dried, pelletized or fresh.
Figure 2:
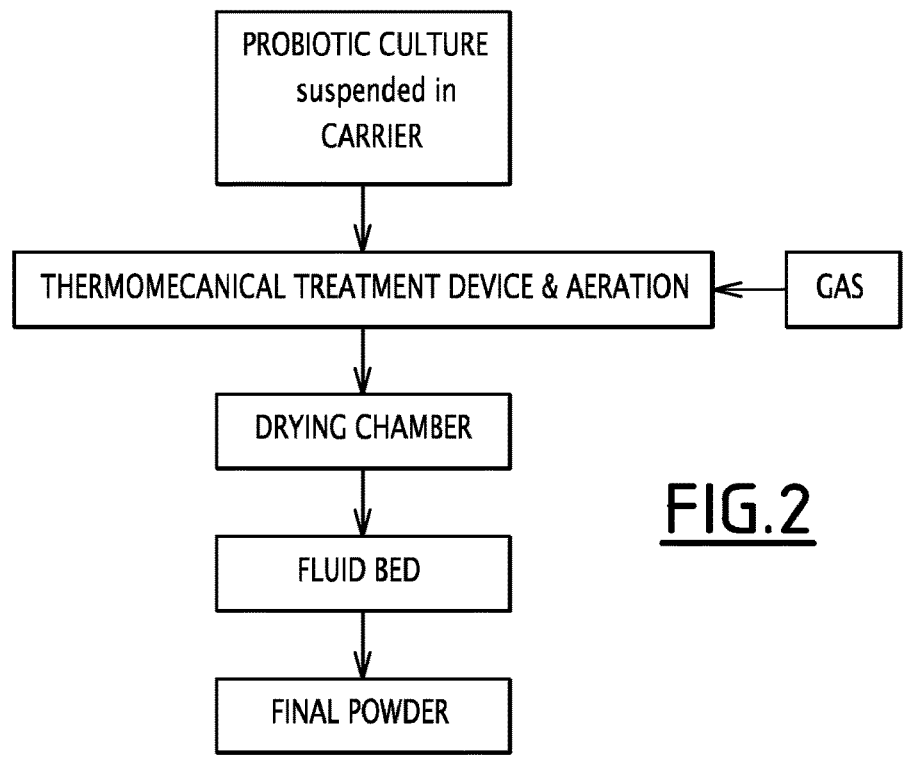
FIG. 2 is a flow chart showing a porous powder production containing cultures according the invention, where the cultures are suspended in the carrier prior to drying.
Figure 3:
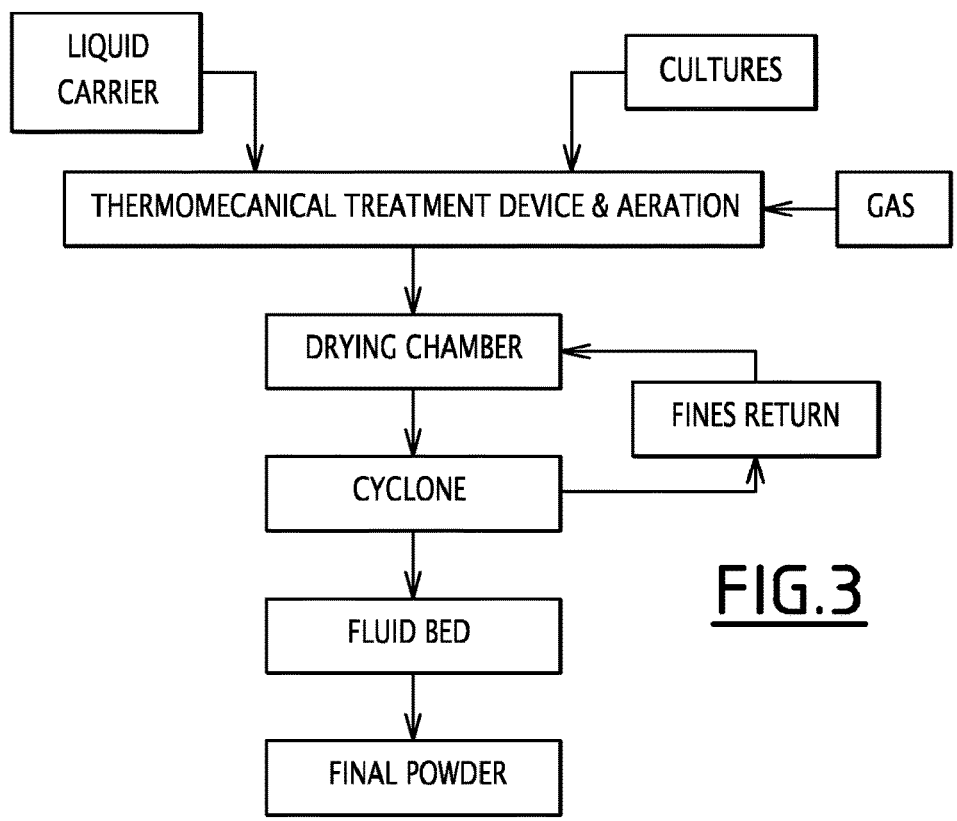
FIG. 3 is a flow chart showing a porous powder production containing cultures according the invention, with use of a cyclone and fines return.
Figure 4:
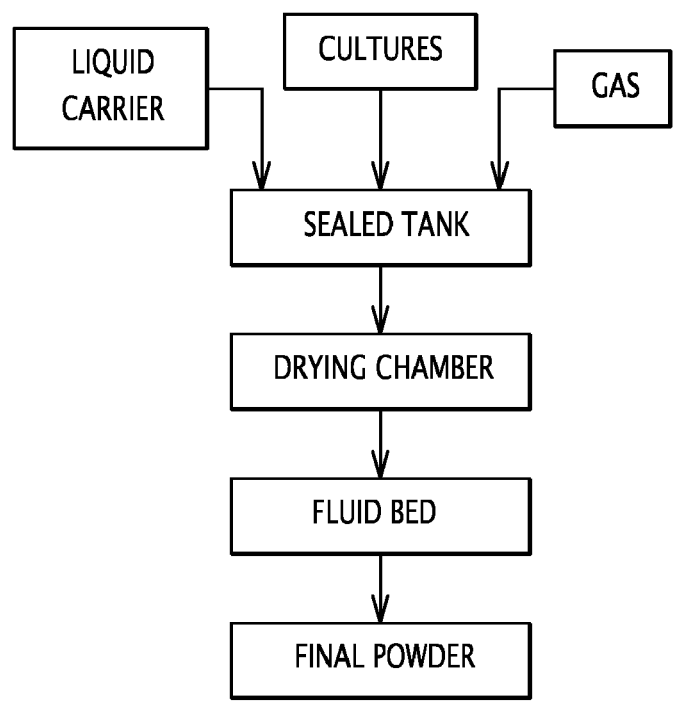
FIG. 4 is a flow chart showing a porous powder production containing cultures according the invention, where the process is a batch process comprising two separated steps.

Referring to FIG. 1, a schematic diagram of a process according to the invention in the form of a flow chart, indicating the device components used. To a thermomechanical treatment device operating at a pressure of about 5 bar and a temperature of about 5 to 40° C., either of the following options can be added (i) a freeze dried culture; (ii) melted pelletized culture; and (iii) cells are grown in a culture and subjected to a shock treatment and a subsequent clarification performed. The cells used in this method are used without the addition of extra protectants and have not as yet been processed. The application of a shock treatment to the microorganism culture is designed to raise the microorganism's resistance to the subsequent drying steps. The clarified culture is then concentrated up to about 15% solids depending on the culture and added to a thermomechanical treatment device operating a pressure of about 5 bar (0.5 MPa) and a temperature of about 15° C.

A liquid carrier composition is then also added to thermomechanical treatment device and the components mixed to form a culture concentrate with a viscosity of about 150 mPa·s. Thus, the starting product for the method according to the invention, i.e. the liquid culture concentrate, needs to be prepared to be sufficiently viscous at the temperature at which this concentrate is formed. In the embodiment of FIG. 1, the concentrate is prepared in the thermomechanical treatment device at a given temperature, this concentrate is treated by the aforesaid device so as to have a minimal viscosity of 150 mPa·s.

The viscous culture concentrate is then advanced by the thermomechanical device and a food grade gas at a pressure under about 1.3 MPa is injected into the concentrate. The gas is partially dissolved and/or dispersed in the concentrate to form a stable foam with a defined porosity and with a density of between 0.6 and 1.2 kg/l, more typically between 0.8 and 1.1 kg/l, and more specifically around 0.85 kg/l. The dissolution and/or dispersion are facilitated by intensive mechanical stirring to disperse the gas in the viscous material to form the stable foam depending on the viscosity of the concentrate. The foam is then subjected to an atomization step to form an atomized product and immediately conveyed to a drying chamber. The drying chamber is an enclosed space where the atomized product is mixed with a drying media. The inlet temperature of the drying media is about 100 to about 200° C. and an outlet temperature is between 50 to 80° C. The atomized product forms small foamy droplets and water migrates from the product to the drying media. The most common drying media is hot air, but the system can be configured to operate under anaerobic conditions where the concentration of oxygen is controlled. Depending on the shape of the chamber, the direction of product movement and the drying media used, the residence time can be controlled. The product is discharged at the bottom of the chamber, at the fluid bed, at the cyclones or at the dust collector with the temperature of the product not exceeding about 50° C. A person skilled in the art will understand, based on the drying characteristics of the product being dried, to when ineffective atomization occurs and a lack of porosity will affect the functionality (density, wettability) of the product. For example, the viability of the cell count, and the rehydration properties of the dried product.

An additional drying step may be used to further reduce the moisture content and the water activity of the product. With this configuration, a fluid bed is used which comprises an enclosed, perforated tray with (hot) air blowing from the bottom through the tray. Vibrations are used to help suspend the moist product on a cushion of air. Compared to the drying chamber which provides quick drying at relatively high temperatures to remove water from the surface of the product, a fluid bed dryer is a moderate drying at medium temperatures over an extended period of time, for example, the residence time can be up to 90 minutes in the fluid bed.

One of the critical advantages of the present invention is the short residence time of the product in the drying apparatus which contributes to the high viability of the processed microorganisms. The residence time of the culture concentrate in the thermomechanical treatment device is approximately 1 minute followed by approximately another 2 minutes in the drying chamber followed by up to 90 minutes in the fluid bed dryer. Thus the total time taken to produce the porous powder product is approximately less than 95 minutes which is significantly shorter than the 48 hours required for freeze drying based system.

Referring to FIG. 2, a schematic diagram of a process according to one embodiment is shown in the form of a flow chart, indicating the device components used. With this embodiment, a process is demonstrated whereby a probiotic or other microorganism culture and suitable carrier composition comprising at least on carbohydrate and at least one protein are added directly to the thermomechanical treatment device via a hopper to form a culture concentrate: the temperature of the culture concentrate in the device is carefully controlled to approximately 5 to 40° C. to assist in the continued viability of the probiotic, and the viscosity of the culture concentrate in the device is more than 150 mPa·s. An example of a suitable thermomechanical treatment device is a twin screw extruder (TSE). Other devices that may be used include a single screw extruder, votators or a scrape surface heat exchangers, etc. It has surprisingly been found that despite the significant shearing and mixing that occurs in the extruder the viability of the culture is maintained.

Pressurized food grade gas is injected into the viscous culture concentrate to form stable foam. The pressure, residence time, temperature, degree of stirring (or mixing) and amount of moisture present in the concentrate will contribute to the amount of gas that is solubilized and/or that is dispersed in the concentrate. The foam is then subjected to atomization whereby there is almost instantaneous release of the gas from the foam resulting in removal of some of the water and the formation of porous powder particles with a defined porosity. The partially dried powder is then discharged into a drying chamber which collects and partially dries the powder product. A drying media, such as hot air, is used in the drying chamber to further remove moisture from the powder product. Where needed, further drying may be achieved by conveying the partially dried product to a fluid bed. Alternatively, a cyclone dryer and then to a small batch dryer could be used (not shown). The residence time of the product in each of these steps (not shown) is the time taken from entry into the extruder to production of the final dried porous product containing the probiotic is approximately 30 minutes.

Referring to FIG. 3, a schematic diagram of a process according to one embodiment is shown in the form of a flow chart, indicating the device components used. With this embodiment, the injection and mixing of the food grade gas are both performed in a thermomechanical treatment device, such as a twin screw extruder to form stable foam. This configuration has the advantage whereby the processing parameters, such as shear rate in the extruder and aeration in the aerator can be independently manipulated. The foam is then subjected to atomization whereby there is almost instantaneous release of the gas from the foam resulting in removal of some of the water and the formation of porous powder particles with a defined porosity. The partially dried powder is then discharged into a drying chamber which collects and partially dries the powder product. A drying media, such as hot air, is used in the drying chamber to further remove moisture from the powder product. With this embodiment, further drying is achieved by conveying the partially dried product to a fluid bed dryer, through a cyclone from which discharged fines are recycled into the drying chamber further enhancing the recovery of solids.

Referring to FIG. 4, a schematic diagram of a batch process according to one embodiment is shown in the form of a flow chart, indicating the device components used. With this embodiment, a batch process is demonstrated whereby a culture, liquid carrier and food grade gas are added to a sealed tank to form stable foam. The foam is then subjected to atomization whereby there is almost instantaneous release of the gas from the foam resulting in removal of at least some of the water and formation of partially dried porous powder particles. Further drying of the partially dried porous powder is then performed on a fluid bed drying apparatus to yield the final porous powdered product.

Figure 5:
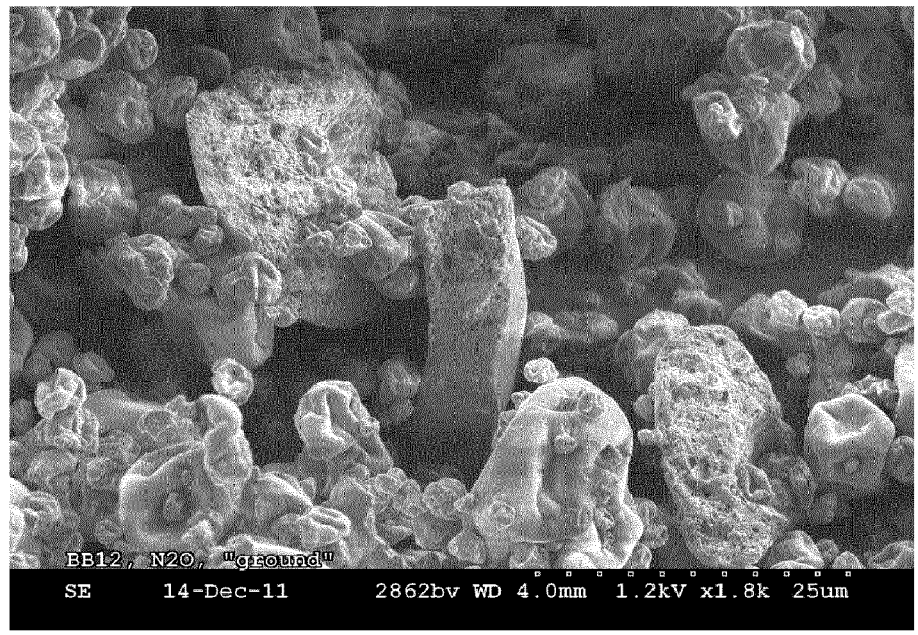
FIG. 5 is a flow chart showing a scanning electron micrograph (SEM) of porous probiotic powder obtained by the method according the invention.

In FIG. 5, a scanning electron micrograph (SEM) of a porous probiotic powder produced by the method of the invention is shown. The strain used was *Bifidobacterium animalis* BB12. The magnification of the picture is 1800. The powder has been grounded to show the inside porosity of the particles. The ground particles show pores of less than 1 μm of diameter. The photo shows also the secondary agglomeration with smaller particles (1-5 μm) that have not been broken during grounding.

It will be appreciated by persons skilled in the art that numerous variations and/or modifications may be made to the above-described embodiments, without departing from the scope of the present invention. The present embodiments are, therefore, to be considered in all respects as illustrative and not restrictive. In some embodiments of the present invention, a culture of a microorganism, which may be a bacterium, yeast, a fungus or a mixture of these microorganisms, is prepared by use of the methods of the invention. A person skilled in the art is capable of selecting the culture medium which is most suited for the growth of the microorganisms.

The culture of microorganisms preferably contains at least $10^7$ colonies of live cells per gram or cfu/g (cfu is the abbreviation for "colony forming unit"). It may also be chosen to concentrate this culture, for example by centrifugation, in order to increase the titre of live cells to at least $10^8$ cfu/g, and preferably to $10^8$-$10^{11}$ cfu/g.

Preferably, there is prepared a culture of at least one microorganism chosen, but not limited, from the group formed by lactic acid bacteria beneficial for human health, for example bifidobacteria such *Bifidobacterium infantis*, lactococci such as *Lactococcus lactis* subsp. *lactis, Lactococcus lactis* subsp. *cremoris, Lactococcus lactis* subsp. *lactic biovar diacetylactis*, streptococci such as *Streptococcus thermophilus, Streptococcus faecalis*, lactobacilli such as *Lactobacillus delbrueckii* subsp. *bulgaricus, Lactobacillus acidophilus, Lactobacillus helveticus, Lactobacillus farciminis, Lactobacillus alimentarius, Lactobacillus casei* subsp. *casei, Lactobacillus delbrueckii* subsp. *lactis, Lactobacillus sake, Lactobacillus curvatus*, pediococci such as *Pediococcus pentosaceus, Pediococcus acidilactici, Pediococcus halophilus*, staphylococci such as *Staphylococcus xylosus, Staphylococcus carnosus*, micrococci such as *Micrococcus varians*; yeasts especially of the genus *Debaromyces, Candida, Pichia, Torulopsis* and *Saccharomyces* such as *Debaromyces hansenii, Candida krusei, Pichia saitoi, Torulopsis holmii, Torulopsis versatilis, Torulopsis etchellsii, Saccharomyces cerevisiae* for example *S. cerevisiae* NCIMB 40612, *Saccharomyces rouxii*; and fungi especially of the genus *Aspergillus, Rhizopus, Mucor* and *Penicillium* such as *Aspergillus oryzae, Aspergillus phoenicis, Aspergillus niger, Aspergillus awamori, Rhizopus oryzae, Rhizopus oligosporus, Rhizopus japonicus, Rhizopus formosaensis, Mucor circinelloides, Mucor japanicus, Penicillium glaucum* and *Penicillium fuscum*.

In some embodiments, the microorganism(s) used in accordance with the methods of the present invention may be chosen from the group comprising the following species: *L. crispatus, L. gasseri, L. salivarius, L. casei, L. plantarum* group, *L. rhamnosus, L. reuteri, L. brevis, L. buchneri, L. fermentum, B. adolescentis, B. angulatum, B. bifidum, B. breve, B. catenulatum, B. longum*, and *B. pseudocatenulatum*.

The invention is particularly appropriate for microorganisms which are sensitive to traditional spray-drying conditions, especially those which are sensitive to heat (heat-sensitive) and/or to the presence of air (preferential anaerobes). Among the microorganisms which are particularly sensitive, there may be included the probiotic lactic acid bacteria. By way of example, there may be used the strain *Lactobacillus acidophilus*.

This culture of microorganisms may further comprise, before or after fermentation, at least one protective chemical agent known to enhance the survival of the microorganisms during the methods of the present invention and/or during the preservation of the powder. Persons skilled in the art have abundant literature on these protective agents. As a general guide, these protective agents typically are vitamins such as ascorbic acid, amino acids or their salts such as lysine, cysteine, glycine and sodium glutamate, proteins or protein hydrolysates which may be obtained from milk or soya, sugars such as lactose, trehalose, sucrose, dextrin and maltodextrin, and fats such as butter fat (butter oil), palm, groundnut, cocoa, rapeseed or soya fat, for example. These protective agents may be added to the culture in an amount of about 0.1 to 80% by weight for example. A core processing step (e.g. homogenization), not described in this patent, may be required to incorporate these protective agents with the culture.

If a powder consisting mainly of microorganisms is desired, the culture of microorganisms may be processed by the methods of the present invention. On the other hand, if a dehydrated food composition, easily dispersible in water and comprising such live microorganisms is desired, it is preferable to dry at the same time all the components of this composition rather than to prepare it by mixing the various constituents already in dry forms. The formation of lumps or of undesirable precipitates is thus avoided.

In one embodiment of the invention, the probiotic component contains from one to six strains, preferably from one to three strains chosen from among the probiotic species mentioned above.

The probiotic may be mixed with a prebiotic material or be part of a symbiotic or synbiotic material.

The term prebiotic means a substance such as a protein, peptide, or carbohydrates that provide nutrients for the probiotic or assist the probiotic.

Usually prebiotics cannot be digested in the upper intestinal tract. Traditional dietary sources of prebiotics include soybeans, inulin sources (such as Jerusalem artichoke, jicama, and chicory root), raw oats, unrefined wheat, unrefined barley and yacon Prebiotic carbohydrates include resistant starch, potato starch or high amylose starch such as Starplus, modified starches (including carboxylated starches, acetylated, propionated, and butyrated starches), non-digestible oligosaccharides such as fructo-, gluco-, xylo-, soyabean-, galacto-, milk-, inulin-, arabinoxylans, arabinogalactans, galactomannans or digestion products of these, but not excluding other oligosaccharides able to exert prebiotic effects.

Throughout this specification the term symbiotic or synbiotic means a combination of a probiotic and a prebiotic which together have a synergistic beneficial effect on human health.

The microorganism cultures useful in the practice of the present invention can be obtained from a variety of sources including, but not limited to:

a liquid microorganisms culture supplied after clarification, centrifugation or ultrafiltration;

a microorganisms culture supplied after freeze-drying, vacuum drying or microwave drying of a culture; and a microorganisms cultures grown inside the storage tank, thermomechanical treatment device, surface heat exchanger, agitated/stirred vessels, etc.

The thermomechanical treatment device useful in the practice of the present invention can take the form of a twin screw extruder, single screw extruder, votators, scrape surface heat exchangers, etc. In certain embodiments, the thermomechanical treatment device is a twin screw extruder (TSE) which allows a good control of the temperature and shear rate. In the case of a co-rotating twin screw extruder, the design of the device can have screw elements interchangeable and in modular form, which allows for a variety of processing options within the same machine. Other devices can be used as single screw extruder (SSE) as long as they can be configured to have at least one transport and/or mixing zone. In a preferred embodiment, the thermomechanical treatment device is a hermetically sealed vessel. For example, the use of twin screw extruder allows for the fine control of temperature, and provides controlled shear rate to liquid concentrates which require shear thinning.

The temperature inside the thermomechanical treatment device is maintained at between 5 to 40° C. Preferably between 25 and 35° C., more preferably at about 30° C.

The carrier composition can be any suitable material which have a Tg inferior to about 70° C. Suitable materials that may be included in the carrier composition include, for example, maltodextrin, high glass transition temperature sugars, i.e sugars having glass transition temperature greater than 55° C. (lactose, maltose and sucrose), water soluble gums (acacia, guar, xanthan), hydroxypropylmethylcellulose (HPMC), alginates, pectin, milk powders, carbohydrates, proteins, etc. Preferably, the carrier composition comprises at least one carbohydrate and at least one protein. Additional excipients may be added to the carrier composition to, for example, further stabilize the microorganism or the product. The choice of suitable excipients will depend on the microorganism and will be known by the person skilled in the art, for example, suitable excipients include full cream milk powder (FCMP), skim milk powder (SMP) and maltodextrin.

The carrier composition can be added as a powder together with an appropriate amount of water to form the culture concentrate with the required viscosity. Alternatively, the carrier composition can be added as a concentrate from an emulsion, an evaporation or rehydration. The carrier composition can also be made from liquid and solid products mixed in the thermomechanical treatment device.

The viscosity of the liquid culture may initially be at least about 50 mPa·s. After an appropriate preparation of the concentrate, for example after process aids and excipients have been added and/or after a first thermomechanical treatment has been implemented, the viscosity of the concentrate at the operating temperature thereof is between 150 mPa·s and 10000 mPa·s, the aforesaid operating temperature of the concentrate being between 5 and 40° C. according to the method of the invention. In practice, the values of viscosity correspond to RVA measurements, i.e. measurements with a Rapid Visco Analyser.

The food grade gas used in the method of the invention is preferably substantially unreactive towards the microorganism being processed and should be suitable for food preparation. The food grade gas may be selected from the group comprising carbon dioxide, oxygen, argon, nitrogen, nitrogen dioxide, air, or mixtures thereof. In a preferred embodiment, the food grade gas is carbon dioxide.

The pressure of the injected gas depends on the desired properties of resultant porous product. In a preferred embodiment, the pressure of the injected food grade gas will change depending the pressure in the thermomechanical treatment device: minimum 0.3 MPa (3 bar) with a typical pressure of 1.3 MPa (13 bar).

The gas may be injected into the thermomechanical treatment device or in a separate aeration device or in both devices. The injected gas can be different and in different amount in both devices.

The foam is then conveyed to a drying chamber where a flash gas expansion occurs after a drop in pressure of at least about 0.2 MPa (2 bar). At this point, the foam is initially subjected to an atomization step whereby it is forced through a small hole and sprayed into the drying chamber into a hot air stream which results in fast drying.

The moisture content of the foam is subsequently reduced in a drying chamber. The foam is forced through a nozzle. The energy to break the foam into small foamy droplets is brought by the atomization gas at between 0.3 to 1.5 MPa (3 and 15 bar). The inlet air temperature is between 100 and 200° C. to obtain an outlet air temperature of approximately 60 to 70° C. The powder temperature at this stage does not exceed approximately 40 to 50° C. While exiting the nozzle, the pressure of the foam goes from approximately 0.3 MPa to 1.2 MPa (0.3 to 12 bar) to approximately atmospheric pressure and some of the gas is released from the foam causing a flash gas expansion. With this expansion, the gas takes out some of the moisture from the product, increases the size of the particles and the gas release creates the porous structure. Then less water has to be removed by the heat and the surface of the particles is larger, thus only a few seconds are needed to dry the powder particles in the drier. The exposed surface area of the particles may be up to two times the surface area of spray-dried particles. The moisture of the powder after this step is between 5 and 10% with total percentage solids of approximately 90 to 95%.

During the final stage of the method, the powder is subsequently dried to a moisture level lower than 5%, preferably lower than 3%, and a water activity of less than 0.25 $A_w$, preferably between 0.1 and 0.25 $A_w$, more preferably around 0.15 $A_w$, when the water activity is measured at 20° C. The temperature is set to decrease the temperature of the powder which should be at ambient temperature at the end of the process. This step can occur along with the drying, while the powder is collected, or in a fluidized bed.

The porosity and total solid control the bulk density of the powder product. Thus, using the method described in Schuck P., Dolivet A., Jeantet R. (2012) *Analytical methods for food and diary powders* (Wiley-Blachwell, Oxford), pages 145-154, the bulk density of the product is advantageously between 0.2 and 0.6 g/cm$^3$, preferably around 0.3 g/cm$^3$. Besides, the powder product may be free-flowing powder, with a particles size between 30 μm to 200 μm. The use of an extruder as the thermomechanical treatment machine enables thermomechanical plasticisation/mixing work to be carried out on the concentrate, allowing, in particular, the mixing, blending and shearing of the concentrate in order to ultimately arrive at a homogenous concentrate. The extrusion machine also has the advantage of allowing continuous treatment process.

Optionally, the final stage of the method is followed by agglomeration to make agglomerated powder.

The present invention is described in greater detail below with the aid of the following non-limiting examples. The percentages are given by weight unless otherwise stated. It goes without saying, however, that these examples are given by way of illustration of the invention and do not constitute in any manner a limitation thereto.

EXAMPLE 1: PREPARATION OF A POROUS *LACTOBACILLUS HELVETICUS* POWDER

A bacterial culture of *Lactobacillus helveticus* (23 kg/h (4% total solids (TS)) and a carrier comprised of a full cream milk powder (35 kg/h (95% TS)) were added respectively through a pump and a hopper, to a twin screw extruder (TSE) operating at 450 rpm, 0.5 MPa (5 bar) of pressure and at 15° C. to form a bacterial culture concentrate at 59% TS. Thorough mixing and mechanical shearing of the concentrate in the twin screw extruder was followed by an injection of $CO_2$ at a pressure of at least 1.3 MPa (13 bar) in the aerator to form a stable foam. The foam was then conveyed to a drying chamber via an atomiser step whereby the pressure is reduced to substantially atmospheric pressure to form a porous powder. Hot air is used as a drying media to remove moisture from the powder at an initial temperature of between 140 to 150° C. (inlet) and an outlet temperature of 68° C. The temperature of the powder was measured at 46° C. A particularly preferred water activity of the powder is 0.15 $A_w$ and the resultant porous probiotic powder has a moisture content of 4.3%.

EXAMPLE 2: PREPARATION OF A POROUS *LACTOBACILLUS RHAMNOSUS* GG POWDER

Bacteria (*Lactobacillus rhamnosus* GG, 5% TS) and a carrier composition comprising a mixture of protein and carbohydrates (reconstituted full milk powder, 95% TS) were added to a twin screw extruder at respective rates of 24 kg/h and 30 kg/h. The two components were subjected to mixing and shearing in the extruder at a screw speed of 320 rpm, pressure of 0.1 MPa (10 bar) and a temperature of 20° C. to form a culture concentrate with total solid of 55% and a viscosity of greater than about 200 mPa·s. Pressurized carbon dioxide at a pressure of 1.3 MPa (13 bar) was then injected into the concentrate and the resultant foam conveyed to a drying chamber via an atomizer where the pressure was let down to atmospheric in the drying chamber. Hot air was used as a drying media at an inlet temperature of 140-170° C. and an outlet temperature of 68° C. to form a porous powder containing the bacteria.

EXAMPLE 3: VIABILITY OF POROSITY DRIED PROBIOTIC—BB12, *L. CASEI* AND *L. ACIDOPHILUS*

The viability of six probiotic samples were tested as follows:

Three liquid samples: Bb12, *L. casei* and *L. acidophilus*, respectively, before drying (~16% TS, provided by MG).

Three porosity dried Bb12, *L. casei* and *L. acidophilus* powders, respectively.

Bb12 were inoculated on reinforced clostridial agar (RCA, pH 6.8). *L. casei* and *L. acidophilus* were inoculated on deMan Rogosa Sharpe Agar (MRS, pH 6.2). The colonies were grown under anaerobic conditions at 37° C. for 48 h. The viability was represented as colony forming unit (CFU) per ml (CFU/ml), for liquid samples, or CFU per gram (CFU/g), for dry samples. To calculate the loss in probiotic viability through drying, the CFU/ml counts of the liquid samples were converted to CFU/g using the total solid content (TS) of the liquid samples using the following equation:

$$(CFU/g)_{before\ drying} = (CFU/ml)_{before\ drying}/TS$$

and the loss of viability through drying was then calculated using the following equation:

$$\text{Loss of viability through drying} = \log_{10}(CFU/g)_{before\ drying} - \log_{10}(CFU/g)_{after\ drying}$$

The viability of the Bb12, *L. casei* and *L. acidophilus* before and after drying was tested and is shown in Table 1.

TABLE 1

Viability of probiotic samples before and after porosity drying

| Sample ID | Viability Before Drying (CFU/ml) | Viability After Drying (CFU/g) | Total Solid of Liquid Samples (TS %) (given by MG) | Viability Loss Through Drying $\log_{10}$ units |
|---|---|---|---|---|
| Bb12 | $(1.27 \pm 0.09) \times 10^{11}$ | $(2.56 \pm 0.20) \times 10^{11}$ | 16.0 | 0.49 |
| Bb12 | $1.2 \times 10^{11}$ | $3.23 \times 10^{11}$ | 16.0 | 0.35 |
| L. casei | $(1.13 \pm 0.33) \times 10^{10}$ | $(1.63 \pm 0.04) \times 10^{10}$ | 16.0 | 0.64 |

The viability of the Bb12 before and after drying was $(1.27 \pm 0.09) \times 10^{11}$ CFU/ml and $(2.56 \pm 0.20) \times 10^{11}$ CFU/g, respectively. The viability of the *L. casei* before and after drying was $(1.13 \pm 0.33) \times 10^9$ CFU/ml and $(1.63 \pm 0.04) \times 10^{10}$ CFU/g, respectively.

EXAMPLE 4: VIABILITY OF POROSITY DRIED PROBIOTIC AFTER 90 DAYS STORAGE AT 4° C.

The viability of porosity dried probiotics was examined after being stored at 4° C. for 90 days as shown in Table 2. It was found that the log reduction in the powder after storage at 4° C. for 90 days was 0.40.

TABLE 2

Viability of processed probiotics

| | Date of drying | Batch size | Gas | Liquid feed cfu/ml | cfu/g | Viability after drying cfu/g | log loss | Viability after storage Length | Temp | cfu/g | log loss/ storage | log loss/ liquid |
|---|---|---|---|---|---|---|---|---|---|---|---|---|
| BB12 | 19 Sep. 2011 | 500 mL | $N_2O$ | 1.4E+11 | 8.4E+11 | 1.8E+11 | −0.68 | 6 months | Fridge | 3.61E+10 | −0.69 | −1.37 |
| Lb. casei | 19 Sep. 2011 | 500 mL | $N_2O$ | 1.8E+10 | 1.1E+11 | 1.9E+10 | −0.77 | | | | | |
| BB12 | 30 Nov. 2011 | 3 L | $CO_2$ | 6.3E+10 | 3.9E+11 | 2.6E+11 | −0.18 | 3 months | Fridge | 2.1E+11 | −0.09 | −0.27 |
| | 30 Nov. 2011 | 3 L | $CO_2$ | 5.0E+10 | 3.1E+11 | 2.7E+11 | −0.06 | 3 months | Ambient | 1.0E+03 | −8.41 | −8.59 |
| BB12 | 19 Dec. 2011 | 3 L | $CO_2$ | 1.3E+11 | 8.1E+11 | 3.2E+11 | −0.40 | 3 months | Fridge | 1.2E+11 | −0.43 | −0.83 |
| | | | | | | | | 3 months | Ambient | 1.21E+07 | −4.43 | −4.82 |
| BB12 | 19 Mar. 2012 | 5 L | $CO_2$ | 6.6E+10 | 4.1E+11 | 1.5E+11 | −0.43 | | | | | |

Note:
Positive log loss numbers are due to standard deviation

EXAMPLE 5: PREPARATION OF A POROUS BIFIDOBACTERIUM ANIMALIS IN BATCH PROCESS

The frozen pellets of bacteria ($10^{11}$ to $10^{12}$ cfu/g) are melted in a water-bath at 40° C. and mixed with a dairy-based UHT concentrate and a pH buffering solution (pH=6.2). The ratio of the mix is 1:1 and its final concentration is 18% total solid. Three liters of concentrate are prepared and poured in a 5 L canister. Once the canister is sealed, $CO_2$ gas is injected until the pressure reaches 0.5 MPa. The canister is then shaken to create a foam. The canister is connected thru its exit line to a nozzle atomizing the product in a drying chamber. The dry powder is collected and further dried on small bench fluid bed drier to reach a water activity of 0.15. The powder is then packaged in aluminium bags with nitrogen. After counting live cells in both the concentrate and the powder, the figures are $8.1 \times 10^{11}$ cfu/g and $3.2 \times 10^{11}$ cfu/g. The loss in viability is 0.40 log.

It will be appreciated by persons skilled in the art that numerous variations and/or modifications may be made to the invention as shown in the specific embodiments without departing from the scope of the claimed invention. The present embodiments are, therefore, to be considered in all respects as illustrative and not restrictive.

The invention claimed is:

1. A method for the production of a porous powder product containing a microorganism, from a liquid concentrate comprising at least one liquid microorganism culture and a carrier composition, the carrier composition comprising at least one carbohydrate and at least one protein, the method comprising the steps of:
   i) preparing the liquid concentrate both to have a temperature of between 5 and 40° C. and to have, at the temperature of the prepared liquid concentrate, a viscosity greater than 150 mPa·s;
   ii) incorporating a pressurized food grade gas into the prepared liquid concentrate at a pressure greater than 0.3 MPa, step (ii) being batch conducted in a hermetically sealed tank containing the liquid concentrate, step (ii) including injecting the pressurized gas into the liquid concentrate in the hermetically sealed tank then shaking the hermetically sealed tank so as to mix the liquid concentrate with the injected gas effective to form a stable foam having a density of between about 0.6 to about 1.2 kg/l;
   iii) conveying the stable foam to an atomizing device in which the pressure of the stable foam is reduced from 0.3 MPa to atmospheric pressure to release the gas from the stable foam for providing a partially dried product; and
   iv) exposing the partially dried product to a drying media to reduce both the moisture content to less than 5% moisture and the water activity to less than 0.25 $A_w$, when measured at 20° C., and to provide the porous powder product, wherein the temperature of the porous powder product in step (iv) does not exceed 50° C.

2. The method according to claim 1, wherein the temperature of the prepared liquid concentrate is from 25 to 35° C.

3. The method according to claim 1, wherein the density of the stable foam is between 0.8 and 1.1 kg/l.

4. The method according to claim 1, wherein the food grade gas is selected from the group comprising carbon dioxide, oxygen, argon, nitrogen, nitrogen dioxide, air, or mixtures thereof.

5. The method according to claim 1, wherein the carrier composition comprises maltodextrin, sugars having glass transition temperature greater than 55° C., such as lactose, maltose and sucrose, water soluble gums such as acacia, guar or xanthan, hydroxypropylmethylcellulose (HPMC), alginates, pectin, milk powders, carbohydrates, proteins, or mixtures thereof, in order to aid the liquid culture concentrate to foam and to dissolve gas.

6. The method according to claim 1, wherein step (iv) comprises a first substep in which the partially dried product is discharged into a drying chamber.

7. The method according to claim 6, wherein step (iv) comprises further a second substep, which is subsequent to the first substep and which is conducted on a fluid bed.

8. The method according to claim 1, wherein, in step (iv), the water activity of the partially dried product is reduced to between 0.1 and 0.25 $A_w$, when measured at 20° C.

9. The method according to claim 1, wherein the bulk density of the porous powder product is between 0.2 g/cm$^3$ and 0.6 g/cm$^3$.

10. The method according to claim 1, wherein the porous powder product is a free-flowing powder, with a particles size between 30 μm to 200 μm.

11. The method according to claim 1, wherein the microorganism is selected from the group comprising bacteria, yeast, fungi and probiotics.

12. The method according to claim 1, wherein step (i) is conducted in a thermomechanical treatment device.

13. The method according to claim 1, wherein step (iv) is followed by agglomeration.

14. The method according to claim 8, wherein, in step (iv), the water activity of the partially dried product is reduced to around 0.15 Aw, when measured at 20° C.

15. The method according to claim 9, wherein the bulk density of the porous powder product is around 0.3 g/cm3.

16. The method according to claim 12, wherein the thermomechanical treatment device is selected from the group comprising a single screw extruder, twin screw extruder, votators, and scrape surface heat exchangers.

17. The method according to claim 1, wherein step (ii) is further conducted in an aeration device, and wherein after being mixed by shaking in the hermetically sealed tank, the gas and the liquid concentrate are further mixed in the aeration device.

18. The method according to claim 1, wherein step (iii) includes connecting an exit line of the hermetically sealed tank to the atomizing device.

19. The method according to claim 2, wherein the temperature of the prepared concentrate is about 30° C.

20. The method according to claim 3, wherein the density is around 0.85 kg/l.

* * * * *